United States Patent [19]

Nielsen

[11] 3,949,737

[45] Apr. 13, 1976

[54] SPIROMETER

[75] Inventor: Carl Philip Nielsen, Chatswood, Australia

[73] Assignee: Allen & Hanburys Limited, London, England

[22] Filed: Dec. 28, 1973

[21] Appl. No.: 429,087

[30] Foreign Application Priority Data
Jan. 4, 1973   Australia.............................. 1799/73

[52] U.S. Cl. ............................. 128/2.08; 272/57 F
[51] Int. Cl.² ........................................... A61B 5/08
[58] Field of Search ................... 128/2.08; 272/57 F

[56] References Cited
UNITED STATES PATENTS

| 767,522 | 8/1904 | Lyttleton | 128/2.08 |
| 829,232 | 8/1906 | Reeves | 128/2.08 |
| 966,050 | 8/1910 | Ramage | 128/2.08 |
| 2,098,280 | 11/1937 | Dornseif | 128/2.08 |
| 2,427,145 | 9/1947 | Koehler et al. | 128/2.08 |
| 2,837,083 | 6/1958 | Lanooy | 128/2.08 |

FOREIGN PATENTS OR APPLICATIONS

| 663,674 | 8/1938 | Germany | 128/2.08 |
| 880,039 | 12/1942 | France | 128/2.08 |
| 880,797 | 1/1943 | France | 128/2.08 |

Primary Examiner—Kyle L. Howell
Attorney, Agent, or Firm—William R. Liberman

[57] ABSTRACT

A device for testing lung function has a body with two chambers axially separated by a partition. An impeller is rotatably mounted in a first one of the chambers on a shaft extending through the partition into both chambers. An air inlet leads into the first chamber so that air can be blown into the chamber tangentially on to the impeller thereby to rotate the impeller. A reduction gear arranged in the second chamber and is driven by the shaft. An indicator is driven by the reduction gear to indicate the number of revolutions of the impeller.

2 Claims, 5 Drawing Figures

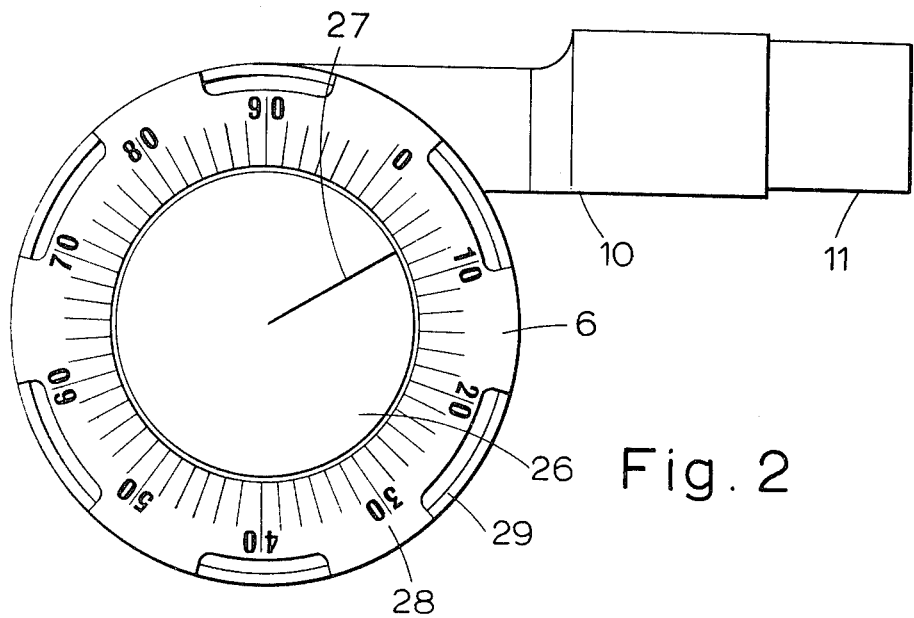
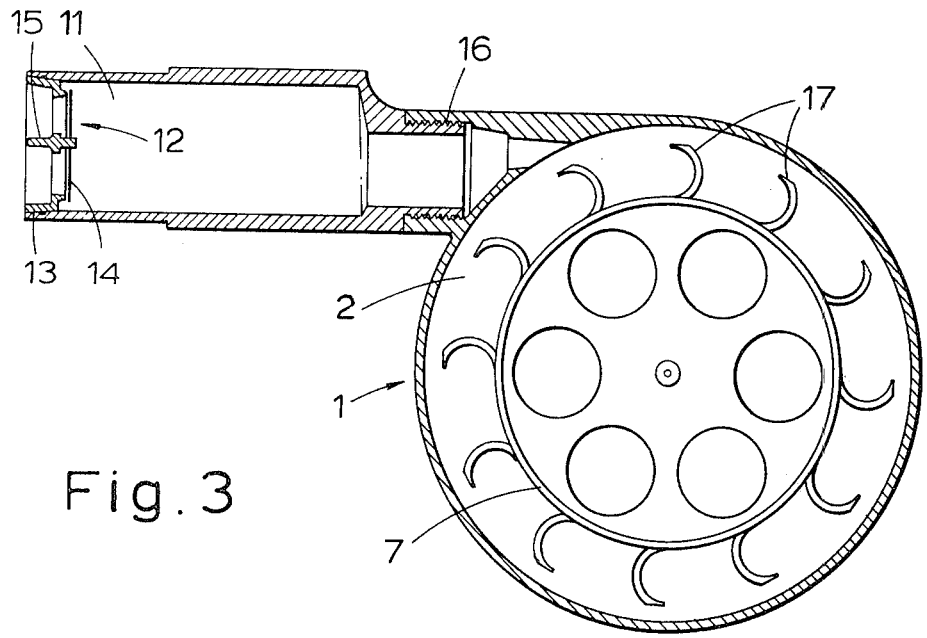

SPIROMETER

BACKGROUND OF THE INVENTION

This invention relates to a device for testing lung function.

Presently available devices for this purpose are the spirometer which is used to record certain standard measurements, including forced expiratory volume in one second ($FEV_1$) and forced vital capacity (FVC), and the Wright peak flow meter, which measures the peak expiratory flow rate (PEFR). $FEV_1$ is the maximum volume of air that is possible for the patient to blow out in 1 second having breathed in as deeply as possible to maximum inspiratory capacity. FVC is the total volume of air that can be breathed out after breathing in to maximum inspiratory capacity.

Such known instruments suffer from the disadvantages of high cost and lack of portability. While they are capable of great accuracy and are necessary if precise quantitative measurements are required, yet there exists a need for an inexpensive and portable device suitable for use in general medical practice, for example in the observation and treatment of asthma sufferers.

Such a device ideally should be sufficiently inexpensive, portable, and easy to use as to be feasibly prescribed for patients to use at home.

BRIEF SUMMARY OF INVENTION

An object of the present invention is to provide such an inexpensive and readily portable device for testing lung function. Accordingly, the invention provides such a device comprising a body, an impeller rotatably mounted in one of the chambers on a shaft, an inlet through which air can be blown tangentially on to the impeller thereby to rotate the impeller, a reduction gear train arranged to be driven by the shaft and an indicator driven by the reduction gear train to indicate the number of revolutions of the impeller.

It has been surprisingly discovered that with this simple apparatus, it is possible to obtain measurements of lung function which closely correlate with readings of $FEV_1$ obtained by the use of a spirometer. Since $FEV_1$ is generally accepted as the most valuable test of lung function, it will be appreciated that the invention represents a considerable advance in economy and simplicity without substantial sacrifice of accuracy.

BRIEF DESCRIPTION OF THE DRAWINGS

In the accompanying drawings which illustrate a preferred embodiment of the invention:

FIG. 2 is an elevation of one side of the spirometer,

FIG. 3 is a partial sectional view taken on the line X—X of FIG. 5,

DESCRIPTION OF PREFERRED EMBODIMENTS

Figure 1:
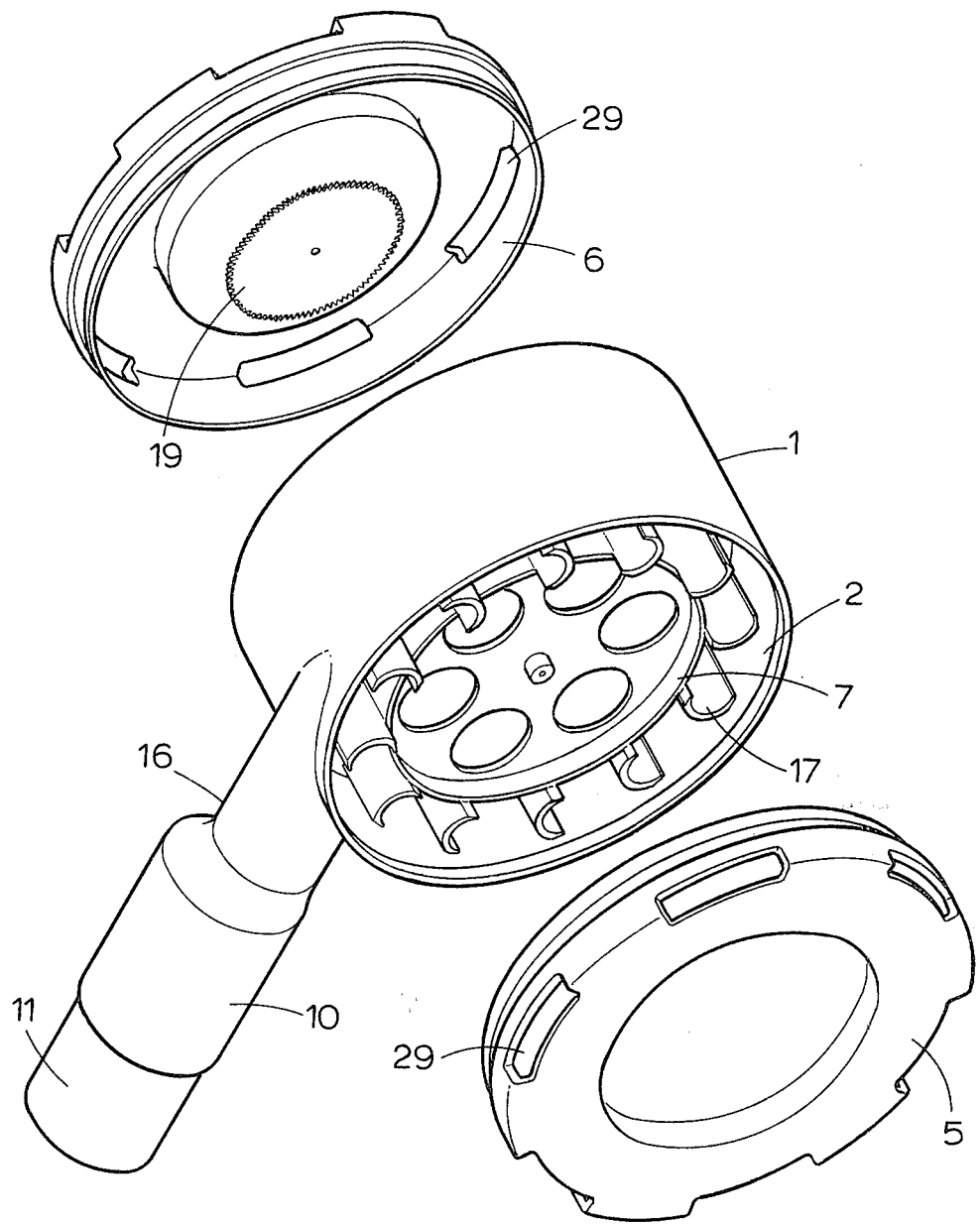
FIG. 1 is an exploded perspective view of a spirometer.
Figure 4:
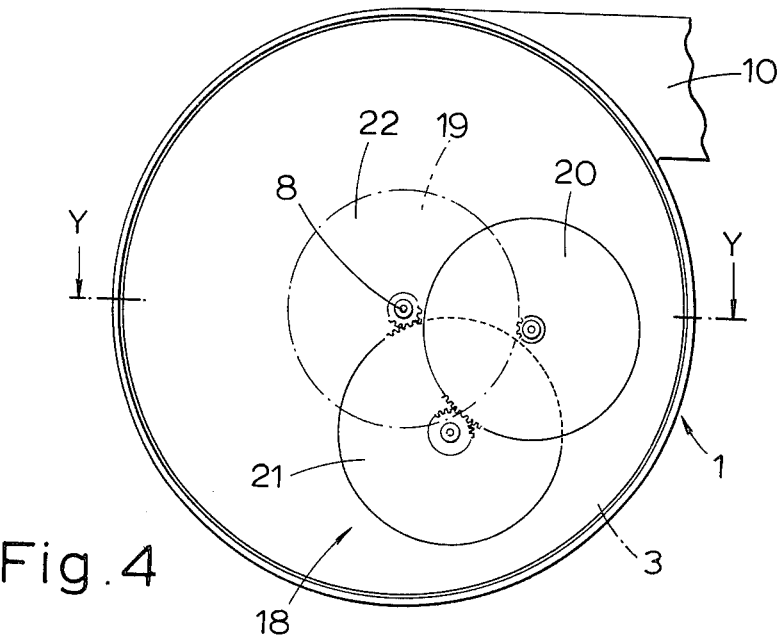
FIG. 4 is an elevation of part of the spriometer with a cover and dial removed.
Figure 5:
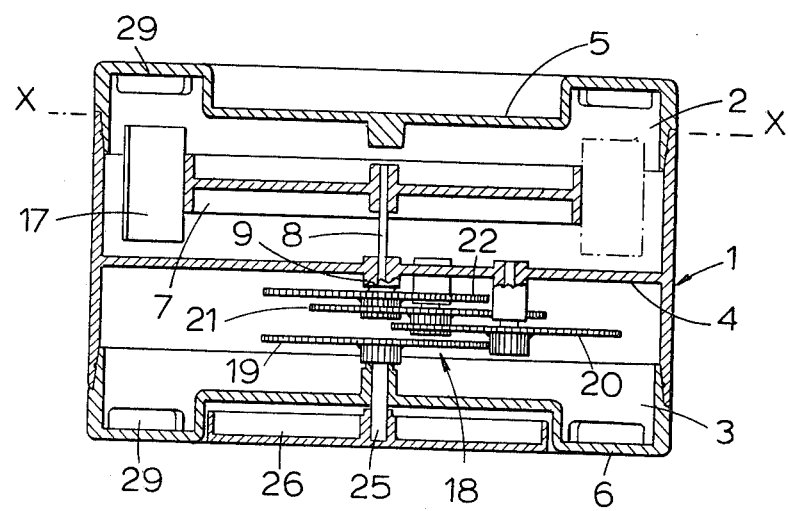
FIG. 5 is a section on the line Y—Y of FIG. 4.

In the illustrated embodiment of the invention, a device for testing lung function comprises a cylindrical body 1 which is open at both ends and is divided into two axially separated chambers 2, 3 by a laterally extending central partition 4. The body is closed at each end by covers 5, 6.

The chamber 2 defined between the partition 4 and the cover 6 encloses an impeller 7 mounted on and locked to an axial shaft 8 which is journalled for free rotation in a boss 9 provided centrally on the partition. This shaft 8 extends into the other chamber 3 of the body as will be more fully described below.

Extending approximately tangentially from the peripheral wall of the body 1 and communicating with impeller chamber 2 is an integral tubular portion 10 which terminates in a portion of reduced outside diameter adapted to receive a standard disposable mouthpiece 11. A non-return valve 12 may be provided immediately inward of the mouth-piece end of this tubular extension although this is not essential. The non-return inlet valve, if provided, conveniently comprises a cylindrical body 13 provided at its inner end with a circular valve seat, a rubber valve member 14 in the form of a disc being mounted on a diametrically extending rib 15 and co-operating with the circular valve seat.

The tubular extension 10 fits within a short mouth 16 extending from the side wall of the body 1 and communicating with the impeller chamber 2 in such a way as to direct air substantially tangentially on to arcuate blades 17 of the impeller 7.

Mounted within the second chamber 3 of the body on the side of the partition 4 opposite the impeller chamber 2 is a reduction gear train 18 of identical gears 19, 20, 21, 22. The final one of these gears 19 is journalled in the adjacent cover 6 co-axially with the impeller shaft 8.

Splined to a shaft 25 of this final gear for rotation therewith, and located on the outside of the relevant cover, there is provided an indicator disc 26 on which a radial line 27 is embossed to function as a pointer.

The annular region of the face of this cover surrounding the indicator is provided with suitably graduated scale 28.

For purposes of economy both covers 5, 6 are identical mouldings, but of course, only cover 5 for the indicator end of the body is provided with graduations. Each cover has provided around its periphery a series of spaced apertures 29, functioning to allow the escape of air from the impeller chamber 2, and to facilitate the cleaning of the device simply by immersion of the device in a cleaning and sterilizing fluid.

The method of blowing appropriate for the device of the present invention may be the same as that which is used in the measurement of $FEV_1$ with a spirometer. The patient is instructed to breathe in as deeply as possible and then to blow out through the instrument as rapidly as he can and to keep blowing until he has reached the limit of exhalation. The method of blowing normally employed in the measurement of PEFR with a peak flow meter has been found, however, to give similar results.

The impeller 7 is started from rest at the commencement of expiration and the reading of the indicator is taken when the impeller has again come to rest.

In a series of tests of a device in accordance with the present invention, normal adults and patients with airways obstruction were tested using the Wright peak flow meter, a spirometer and the device of the present invention. It was found that with the normal adults with a wide range of lung function ($FEV_1$ between 2.1 and 5.7 l/sec.) the relationship between the readings of the device of the present invention and $FEV_1$ had a correlation co-efficient of 0.91 and a Standard Error 20.0. In the case of the 65 patients with airways obstruction, with a range of $FEV_1$ between 0.5 and 4.5 l/sec, the relationship between the readings of the device of the present invention and $FEV_1$ showed a correlation coefficient of 0.94 and a Stardard Error of 16.8.

To avoid the necessity of providing some form of return mechanism which would interfere with the simplicity of the device, the covers 5, 6 (or at least the cover 5 carrying the graduations) are mounted on the respective ends of the cylindrical body 1 so that they may be rotated with respect to the body and therefore with respect to the stationary impeller 7 to re-set the zero of the scale 28 with the embossed pointer 27 on the indicator disc 26. Naturally, the fit of the covers with the body is sufficiently tight to prevent relative rotation of these two parts while the device is in operation. Alternatively, the disc can be re-set to zero by simply returning the disc 26 to the zero position manually.

Apart from the shafts, which should be of stainless steel, and the rubber non-return valve element, all the remaining components of the device are preferably moulded from an acetal resin plastics material. Such material has low hygroscopy and good dimensional stability.

What is claimed is:

1. Combination means for indirectly determining the forced expiratory volume in 1 second ($FEV_1$) of a subject, the combination comprising:
   1. a device for measuring lung exhalation comprising a body defining a cylindrical interior volume; a partition axially dividing the interior volume into two cylindrical chambers; a shaft rotatably mounted centrally in the partition and extending axially into both chambers; an impeller in one of said chambers having an arcuately vaned periphery and being mounted on and rotatable with the shaft; tubular inlet means for the exhalation of a subject connected to the body and opening into said first chamber, and inlet means extending outwardly from the chamber and substantially tangentially of the vaned periphery of the impeller, whereby exhalation flowing through the inlet will impinge upon the impeller and cause it to rotate; a cover for the first chamber; reduction gear train means in the second of said chambers driven by the shaft and comprising a final gear; a second cover for the second chamber; a second shaft rotatably mounted in the cover and extending axially into the second chamber and externally of the body and an indicator mounted on and rotatable with said second shaft and with respect to the second cover, whereby rotation of the impeller causes slower rotation of the indicator relative to the cover, and
   2. means for converting the angular distance travelled by the indicator with respect to the second cover into the forced expiratory volume in one second for a subject exhaling into the inlet means.

2. The combination means of claim 1 wherein the second cover comprises a suitably graduated scale surrounding the indicator to enable measurement of the angular movement of the indicator and thus provide a measurement of $FEV_1$ values.

* * * * *